US007655269B2

(12) United States Patent
Mayer et al.

(10) Patent No.: US 7,655,269 B2
(45) Date of Patent: Feb. 2, 2010

(54) INTEGRATED NANOMECHANICAL SENSOR ARRAY CHIPS

(75) Inventors: Theresa S. Mayer, Port Matilda, PA (US); Christine D. Keating, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 397 days.

(21) Appl. No.: 10/423,832

(22) Filed: Apr. 25, 2003

(65) Prior Publication Data

US 2003/0215865 A1  Nov. 20, 2003

Related U.S. Application Data

(60) Provisional application No. 60/377,099, filed on Apr. 26, 2002.

(51) Int. Cl.
  *G01N 1/33* (2006.01)
(52) U.S. Cl. ............... 427/2.13; 435/285.2; 435/287.1; 427/8; 427/10; 977/702; 977/877
(58) Field of Classification Search ............... 436/164, 436/171, 524, 526, 528; 422/55, 57; 333/186, 333/197; 423/447.3; 257/14; 438/22
See application file for complete search history.

(56) References Cited

U.S. PATENT DOCUMENTS

| 5,620,854 | A | | 4/1997 | Holzrichter et al. ............ 435/6 |
| 6,159,742 | A | * | 12/2000 | Lieber et al. ................ 436/164 |
| 6,287,765 | B1 | | 9/2001 | Cubicciotti ................... 435/6 |
| 6,459,095 | B1 | * | 10/2002 | Heath et al. ................... 257/14 |
| 6,803,840 | B2 | * | 10/2004 | Hunt et al. ................... 333/186 |
| 2002/0117659 | A1 | * | 8/2002 | Lieber et al. ................. 257/14 |
| 2002/0167374 | A1 | | 11/2002 | Hunt et al. .................. 333/186 |
| 2003/0234465 | A1 | * | 12/2003 | Chen et al. ................... 264/108 |

* cited by examiner

*Primary Examiner*—Nelson Yang
(74) *Attorney, Agent, or Firm*—Gifford, Krass, Sprinkle, Anderson & Citkowski, P.C.

(57) ABSTRACT

The invention provides sensor, preferably biosensor devices and method of fabrication. The devices have significant advantages over the prior art methods having compatibility with future trends in clinical diagnostics and chemical detection. The underlying principle involves the integration of nanometer diameter, micron long metal or semiconductor rods onto a substrate to form a suspended nanomechanical cantilevers. The cantilever rods are rigidly attached to the substrate on one or both ends, and resonate at a characteristic frequency depending on the diameter, length, and stiffness of the rod. The metal or semiconductor rods are integrated onto the substrate using electrofluidic or fluidic assembly techniques. A receptor coating is placed on the metal or semiconductor rods prior to or following rod alignment using self-assembly chemistries. Sensing is accomplished when the target agent binds to the receptor substance, causing a change in the mass of the cantilever rod, and a corresponding change in the resonant frequency. This change in resonant frequency can be detected using an electrical readout. The sensing circuitry is integrated with CMOS or TFT technologies to form compact multi-analyte senor arrays on single crystal silicon, glass, or polymeric substrates. Circuits can also be included on the substrate to transmit the array data via wireless methods to a remote workstation for analysis. Devices may be integrated on chips with other analysis devices.

16 Claims, 9 Drawing Sheets biosensor operation; dynamic mode

A

B

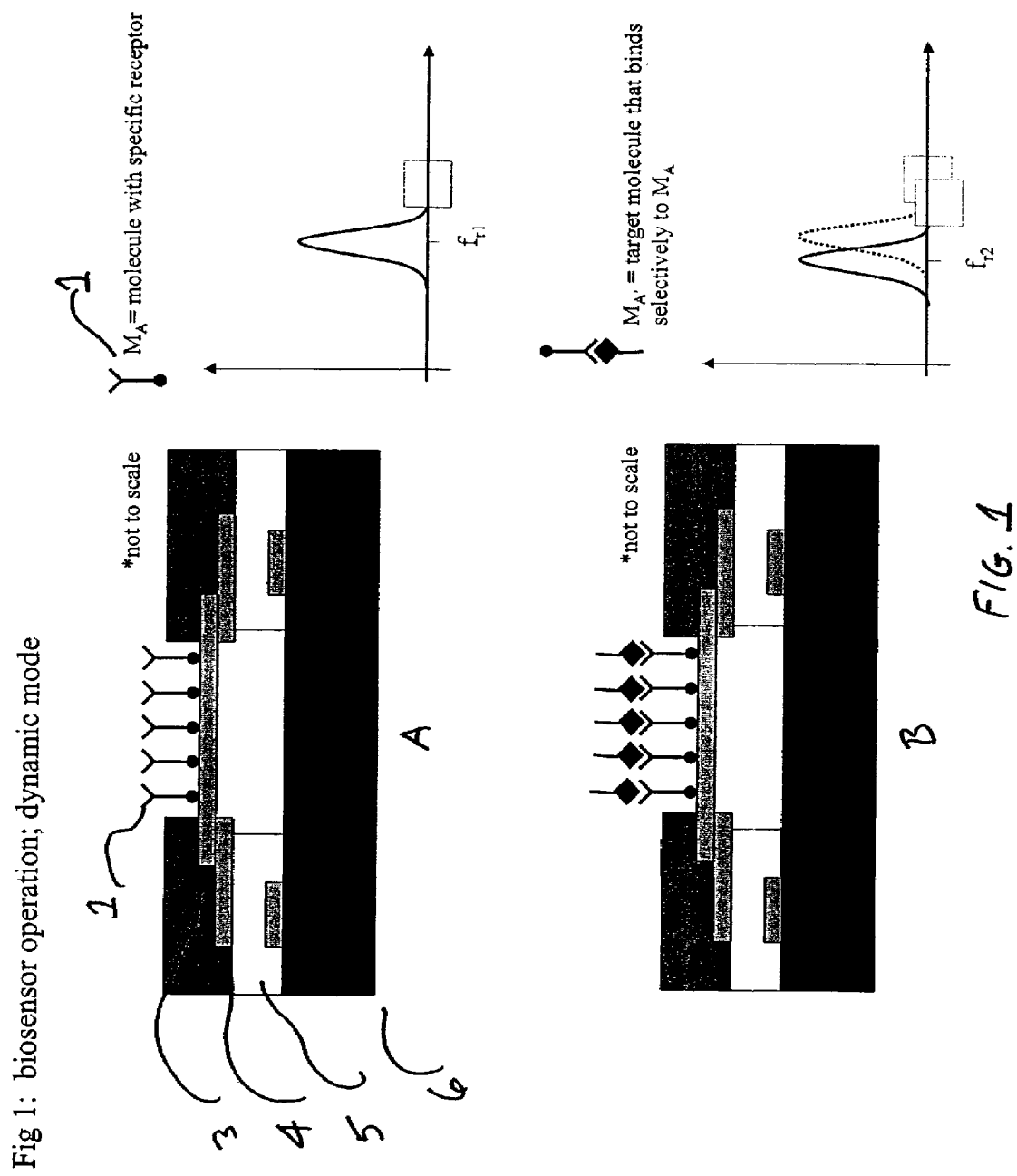
Fig 1: biosensor operation; dynamic mode

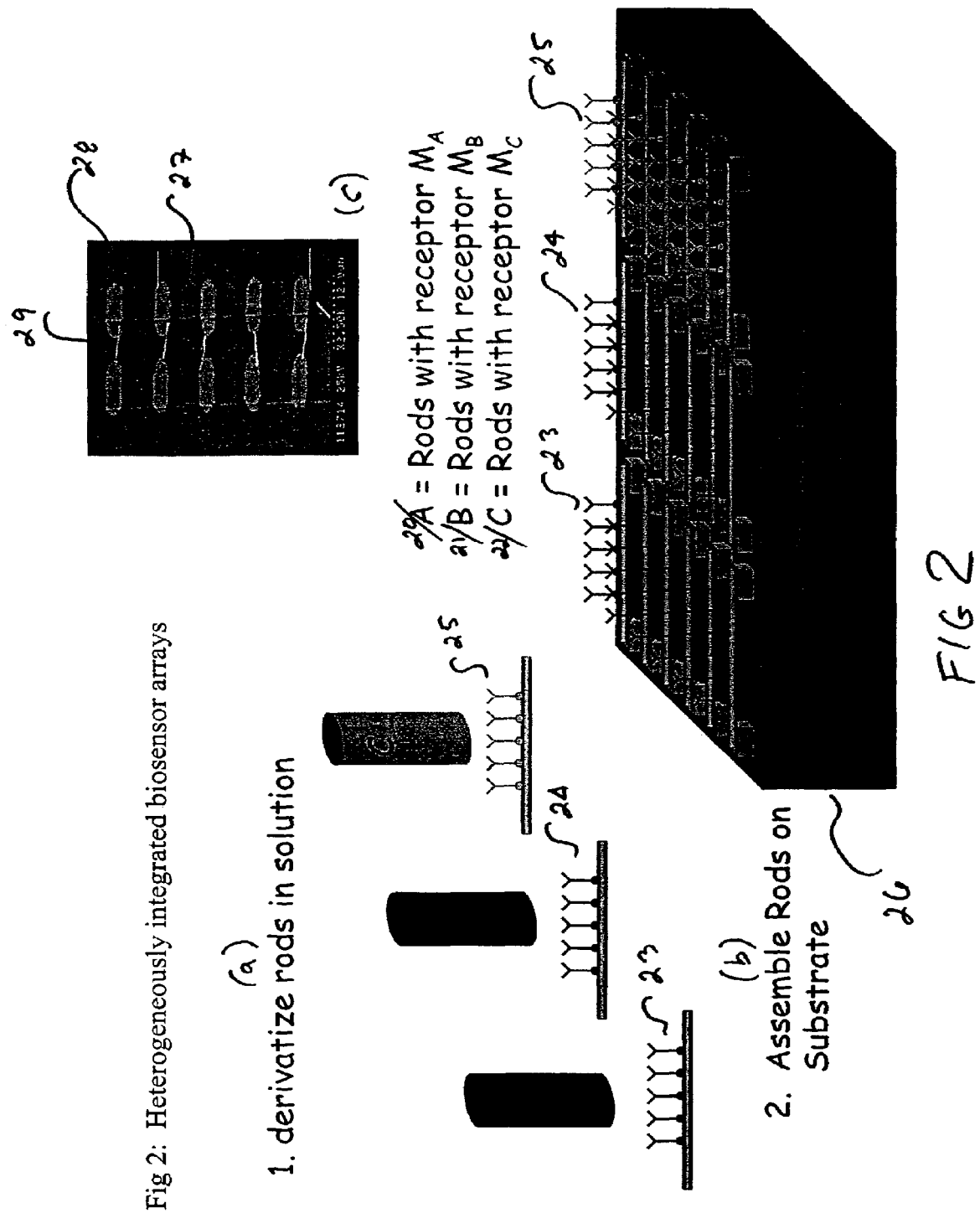

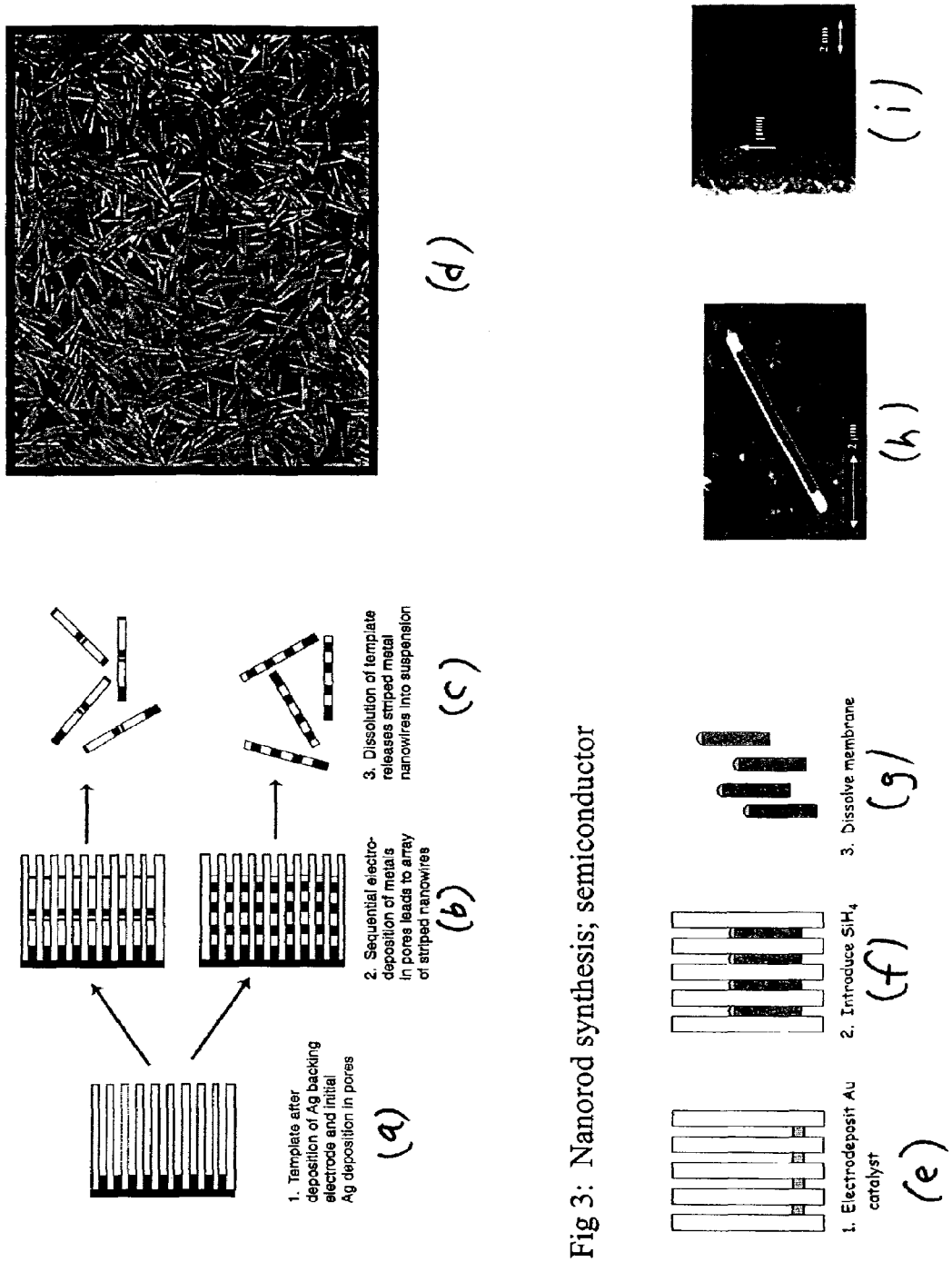
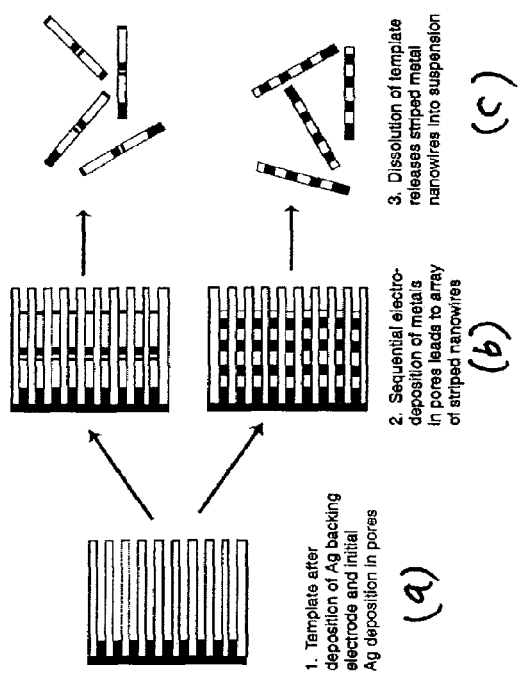
Fig 3: Nanorod synthesis; metal
Fig 3: Nanorod synthesis; semiconductor

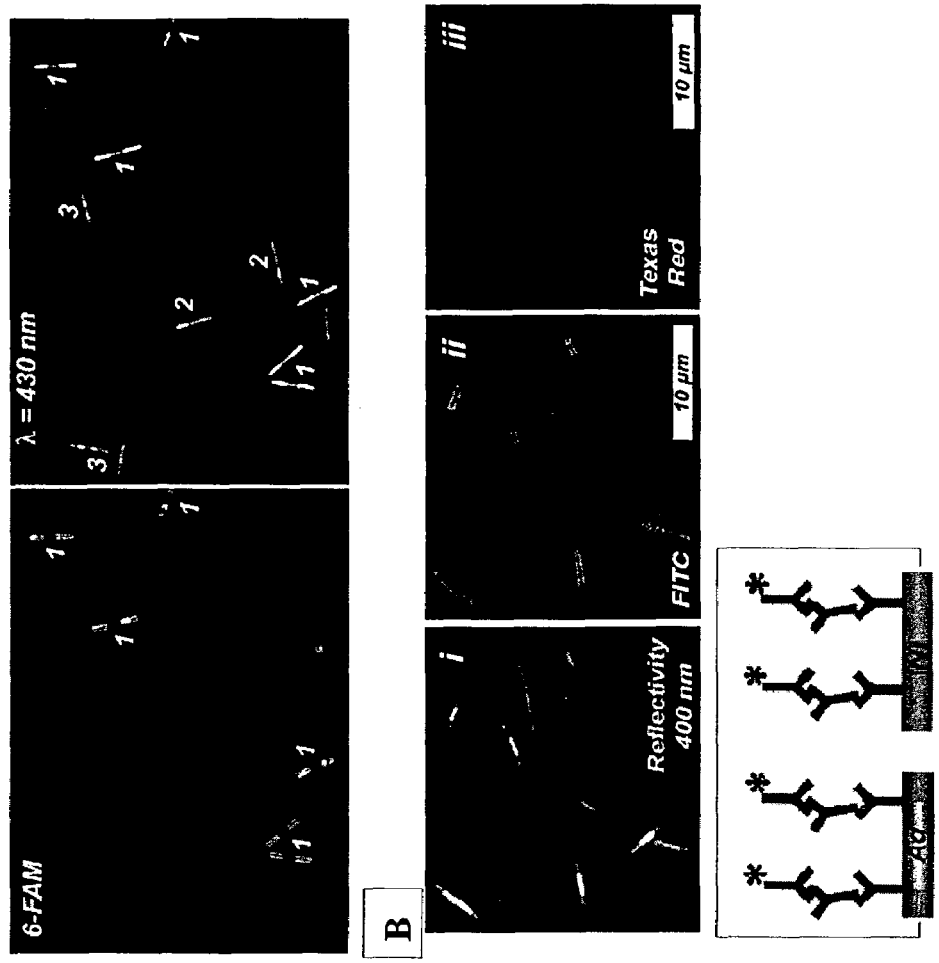
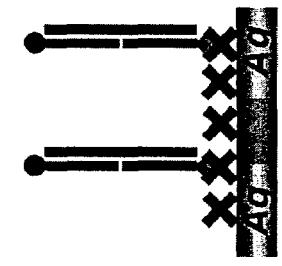
Fig 4: Nanorod derivitization

Fig 5: Nanoparticle amplification

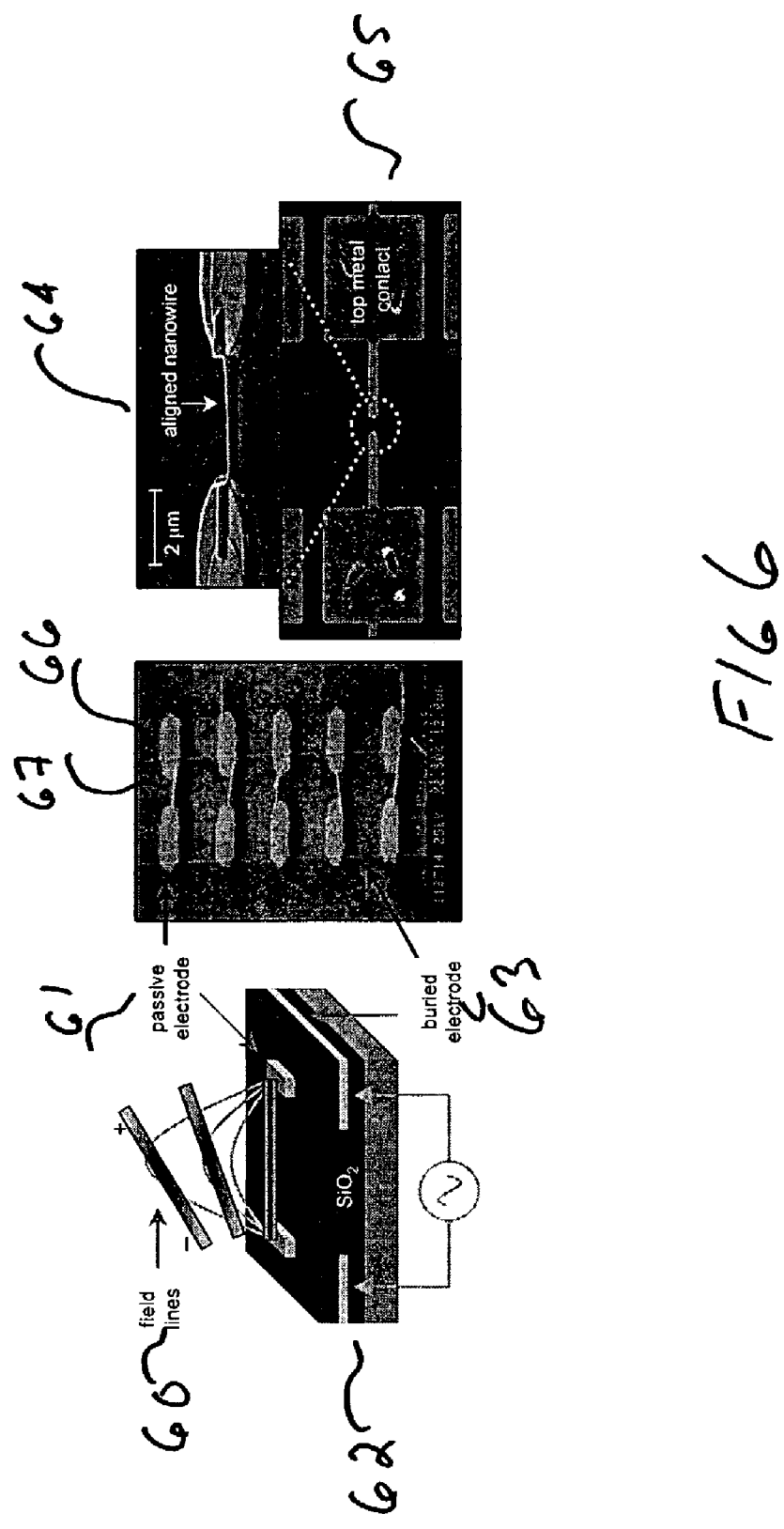
Fig 6: Electric field assisted assembly and integration

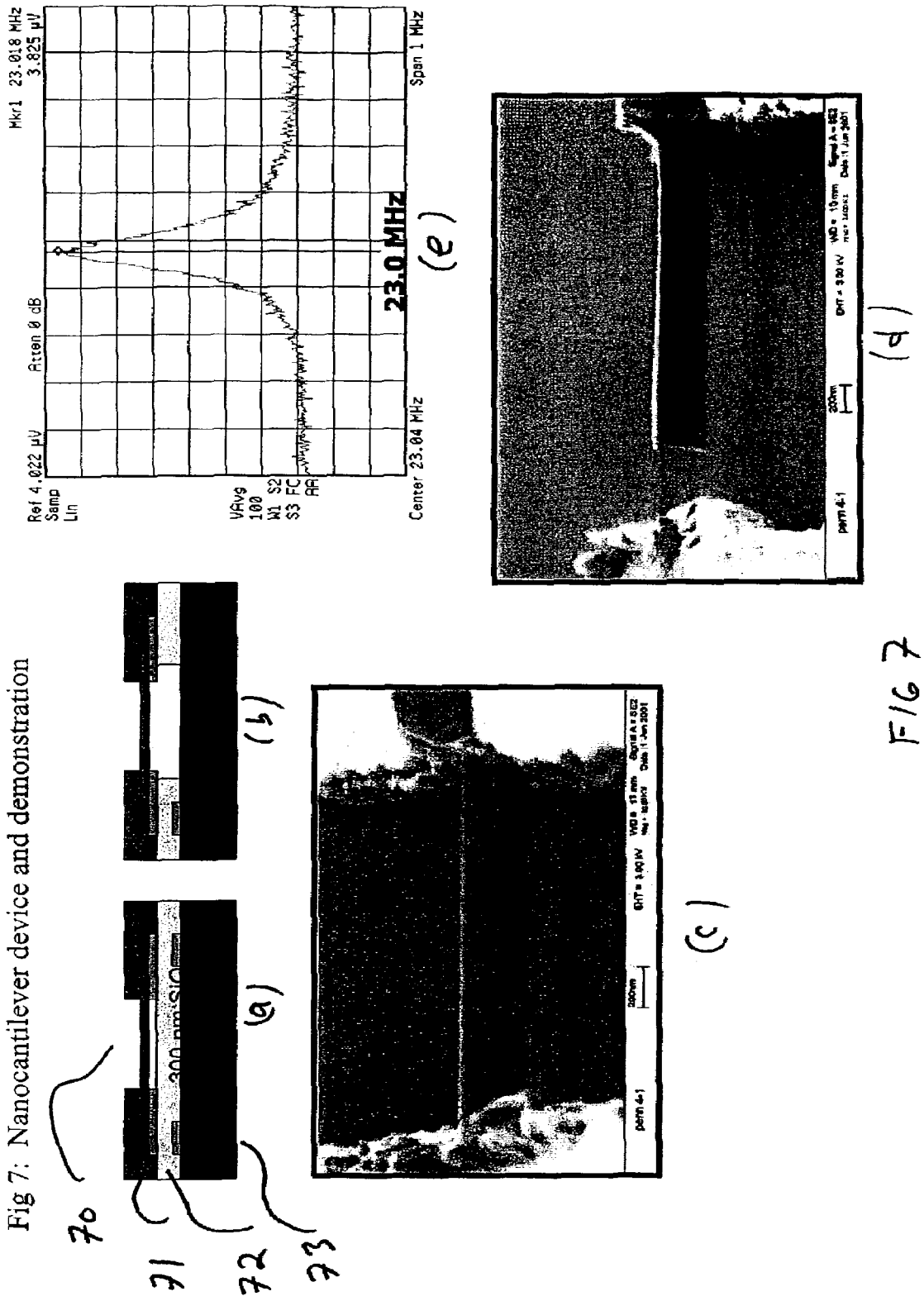
Fig 7: Nanocantilever device and demonstration

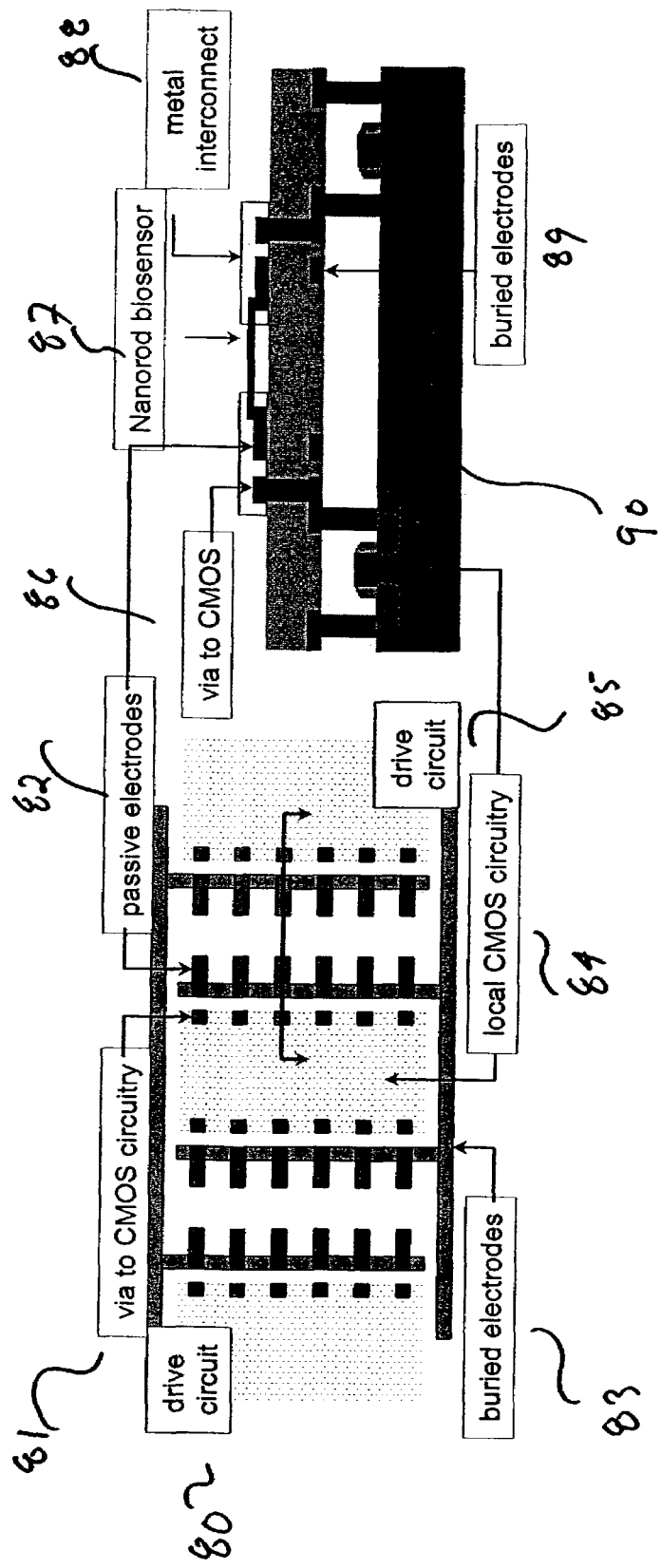
Fig 8: Nanorod integration with CMOS electronic circuit

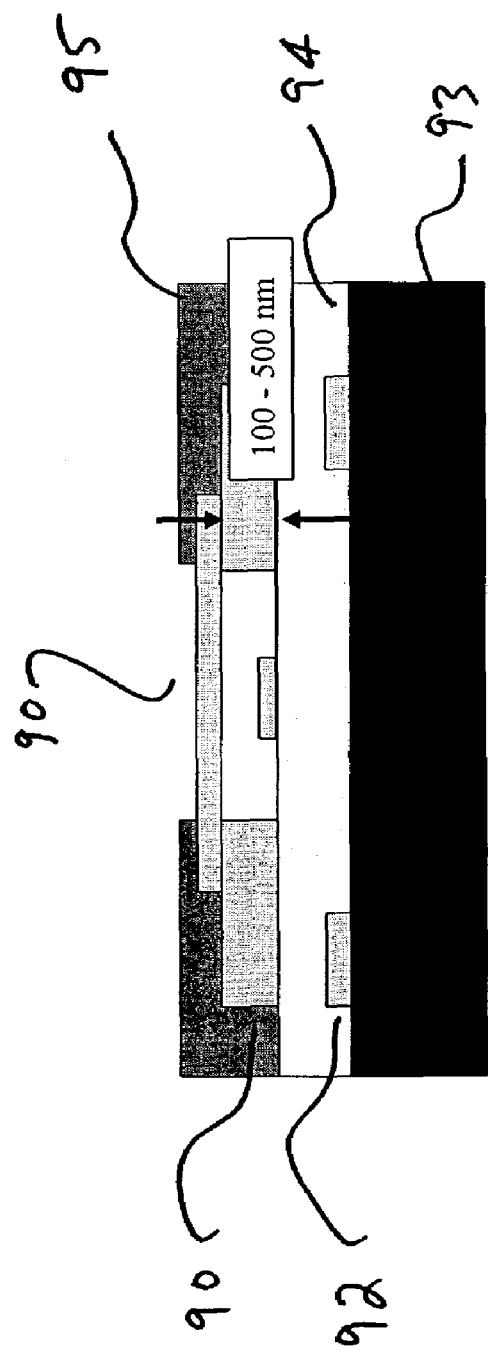
Fig 9: Example nanocantilever biosensor cross section

INTEGRATED NANOMECHANICAL SENSOR ARRAY CHIPS

This application claims priority from U.S. Provisional Application Ser. No. 60/377,099 filed Apr. 26, 2002.

This application was supported by ONR/DARPA grant number N00014-98-1-0846. Accordingly the US government may have certain rights in this invention.

BACKGROUND OF THE INVENTION

1. Field of the Invention

The present invention relates to the field of heterogeneously integrated sensor arrays, preferably biosensor arrays. In particular, the invention relates to nanomechanical cantilever type biosensors for detecting target-receptor molecule binding, which produce an electrical detection signal upon change in cantilever mass or static deflection. The invention also relates to the manufacture of nanomechanical cantilever biosensor arrays by parallel assembly of many different biomolecule derivatized nanorods onto single silicon or thin-film electronic circuits using "bottom-up" integration strategies.

2. Description of the Prior Art

During the past decade, there: has been an increasing interest from the commercial and government sectors to develop on-chip integrated biosensor arrays that can selectively report the presence and quantity of specific biomolecules contained in sample populations. Examples of such populations range from cells and model organisms for pharmaceutical and genome research to samples of the environment for pathogens and biological warfare agent detection. In the case of genome research, it is necessary to discover gene sequences that provide a blueprint of the cell or organism through systematic identification of known and predicted genes. It is also of great interest to use the so-called genomic arrays for gene expression monitoring and for screening sequence variants or mutations. For these applications, it would be desirable to survey >1 Mbit of genomic information on a single chip that is only a few $cm^2$ in area. In contrast, biosensors used to screen pathogens may have relaxed requirements on the number of different biomolecules that must be sensed simultaneously, while placing greater emphasis on detection time, minimum detection levels, field durability, overall system size, and cost.

Most biosensor platforms are based on the extremely selective recognition principles inherent in biological systems. Bioreceptors that have been used as sensing elements include biomolecules such as antibodies, enzymes, and nucleic acids. When a receptor undergoes a binding event with a target biomolecule, the information collected by the sensing element regarding the receptor-target attachment must be converted into a signal that can be easily measured. There are a number of transduction mechanisms that can be exploited for converting this attachment information, including optical, electrochemical, magnetic, and mass sensitive measurements. The choice of the particular bioreceptor/transducer combination will ultimately impact biosensor figures of merit such as detection sensitivity, selectivity, integrability, scalability, and cost.

Most commercially available integrated biosensors rely on optical sensing of antibody-antigen interactions and complementary DNA hybridization. One example involves fluorescently-tagged target DNA that hybridizes with complementary receptors on the sample. DNA microchip arrays are based on this principle, and have increased rapidly in sophistication and density as a result of a number of recent technological developments. First, non-porous substrates such as glass were introduced, facilitating miniaturization of fluorescence detection. Second, semiconductor photolithography techniques were adapted to control the spatial synthesis of oligonucleotides. Currently, these "gene chips" can contain as many as 400,000 distinct oligonucleotides, where each sensor element occupies ~20 $\mu m^2$. These developments have made possible large-scale scientific studies on gene expression (i.e., what the protein product of the gene does) and, to a lesser extent, gene variation (i.e., identifying SNPs). While the progress on "gene chips" has been impressive, continued miniaturization will require significant advances in improving the sensitivity of fluorescent labeling and optical detection techniques. It is also unlikely that extensions to this technique will provide quantitative data regarding the concentration of particular DNA sequences, especially for extremely low concentrations of DNA. Finally, because non-specific binding of SNPs is unacceptably high even with short oligonucleotides, further refinements are needed before gene variations can be thoroughly studied using these biosensor arrays.

There are several other techniques that also rely on fluorescent tagging and/or optical readout, which have not matured commercially to the level of the "gene chip". These include surface plasmon resonance, evanescent dielectric waveguides, self-encoded beads, and self-encoded nanoparticles. The first two are capable of collecting kinetic data for hybridization in situ due to their surface selectivity. The last two encode sequence information optically rather than spatially (as in gene chips): polymer beads with fluorophores of distinct wavelengths, and nanometer-scale rods with bars of metals having high contrast. Self-encoded nanoparticles remove many of the limitations associated with transport of target molecules to the sensor elements on planar arrays by suspending the nanoparticles in solution during hybridization and readout. However, each of these techniques still requires sophisticated optical detection, which may limit their utility in certain applications.

A technique that has the potential to enhance the selectivity and sensitivity of DNA microarrays labels oligonucleotide targets with metal nanoparticles rather than fluorophores. In this scheme, a three-component "sandwich assay" is used whereby the target hybridizes with complementary receptors immobilized on the sensor surface and on the nanoparticles. Hybridization is detected by first increasing the size of the nanoparticles through Ag electroless plating and then by optically scanning the sample using a flatbed scanner to detect changes in optical contrast between different sensor elements. This work also demonstrates that nanoparticle labels improve significantly the selectivity of oligonucleotide hybridization with single base pair mismatches.

To overcome drawbacks of optical sensing, several groups have initiated research on biosensors that detect the presence of target biomolecules based on magnetic, electrical, or mass sensitive transduction. The bead array counter biosensor uses DNA-functionalized magnetic nanoparticles as the target probe and complementary DNA-covered magnetoresistive materials as the receptor/transducer. When target and receptor DNA hybridize, the magnetic particles bind to the sensing element and modify the local magnetic field. This change is measured electrically by monitoring the resistance of the element, where the resistance is proportional to the number of hybridized beads on the element. Unlike sensors that use optical readout, electronic functions can be integrated directly on chip with the sensing element.

Mass sensitive biosensors are among the newest and perhaps one of the most promising approaches for applications requiring high-density, on-chip integration of receptor/transducer and signal/data processing functions. It has been demonstrated that large-area quartz crystal microbalances (QCMs), which measure the shift in resonant frequency of a quartz crystal oscillator due to mass changes by target-receptor binding, are up to 100 times more sensitive than DNA microarrays. While it is difficult to scale and integrate QCM technology, two groups have investigated a related approach that uses silicon micromachined cantilevers as strain- or mass-sensitive transducers. Receptor DNA was attached to the top surface of 100×500 $\mu m^2$ cantilevers and the static deflection of the cantilever due to surface stress induced during DNA hybridization was measured optically. Deflections of 17 nm were induced when large (400 nM) concentrations of complementary target DNA were analyzed.

Additionally, some patent prior art has addressed the need for integrated biosensors. Two published patent documents in the field of micromechanical biosensors are U.S. Pat. No. 6,289,717 to Thundat et. al. and PCT publication WO 98/50773 to Charych et. al. Thundat discloses a sensor apparatus comprising a microcantilevered spring element having a coating of a detector molecule wherein the spring element bends in response to a binding event. Similarly, Charych uses a microfabrication process to produce a thin deposition of piezoelectric material to produce a microcantilever that responds to a binding event with an electrical signal.

Despite prior art teachings there continues to be a need for heterogeneously integrated biosensors having improved properties and advantages. This is the need addressed by the present invention. While prior art practice for integrated mass sensitive biosensing is focused on cantilever structures based on standard silicon micromachining techniques, the present invention describes a nanomechanical cantilever type biosensor that offers improved sensitivity, selectivity, and dynamic range. The present invention also describes methods for producing biosensor arrays based on parallel assembly of many different biomolecule derivatized nanorods onto silicon or thin-film electronic circuits using bottom-up integration strategies.

Accordingly, it is an object of the present invention to provide a new an improved method of making nanomechanical devices.

Another object of the present invention is to provide a method of making nanometer scale transducers using "bottom-up" integration.

Another object of the present invention is to provide a method of making nanomechanical transducers having electrofluidic or fluidic directed assembly.

A further object of the invention is to provide a nanoscale transducers that are useful as chemical or biological sensors.

Yet another object of the invention is to provide nanoscale transducers having nanomechanical cantilevers providing sensitive and selective detection capability.

These and other objects and advantages of the invention and equivalents thereof, are described and provided in the drawings and descriptions that follow and manifest in the appended claims.

SUMMARY OF THE INVENTION

The invention is a new sensor, preferably a biosensor, and corresponding bottom-up fabrication strategy with significant advantages over the prior art methods having compatibility with future trends in clinical diagnostics and chemical warfare agent detection. The underlying principle involves parallel assembly of many different biomolecule derivatized nanometer diameter, micron long metal, semiconductor, or insulating rods onto a substrate to produce heterogeneous arrays of nanomechanical cantilever biosensors. The term "cantilever" as used in this patent application, we mean either fixed-free or fixed-fixed wires/beams. The cantilever rods are rigidly attached to the substrate on one or both ends, and resonate at a characteristic frequency depending on the diameter, length, and stiffness of the rod. Many different metal, semiconductor, or insulating rods are assembled onto the substrate in parallel using bottom-up integration strategies. The term "rod" or "nanorod" as used herein is a rod-like structure having a nanometer diameter and a micron-size length. Each rod can be derivatized with a different receptor coating (e.g. biological or chemically sensitive molecules or polymers) that is placed on the metal, semiconductor, or insulating rods using nonspecific direct adsorption or specific self-assembly chemistries prior to rod assembly. Sensing is accomplished when the target molecules bind to the receptor coating, causing a change in the mass of the cantilever rod, and a corresponding change in the resonant frequency. The target binding can also be measured via a static deflection of the nanorod in environments where the mechanical resonance of the rod may be damped. This change in resonant frequency or static deflection can be detected using an electrical readout via capacitive, piezoelectric, or electromagnetic approaches. Nanomechanical cantilever biosensors that have been derivatized with different receptor coatings can be integrated in parallel onto CMOS or thin-film electronic circuits to form compact multi-analyte biosensor arrays on single crystal silicon, glass, or polymeric substrates.

The invention provides a method for producing a nanomechanical device comprising: applying onto a patterned substrate at least one nanorod derivatized with receptor material; aligning the at least one derivatized nanorod on said patterned substrate; and integrating the at least one nanorod with said patterned substrate so as to form an integrated nanocantilever structure, thereby producing a nanomechanical device. Nanorods are selected from the group consisting of: metals, semiconductor materials, insulator materials, dielectric materials, piezoelectric materials, and any combinations thereof. Nanorod materials are Au, Pt, Pd, Ag, Pb, Ni, Rh, Co, CdSe, Si, and any combinations thereof. Nanorod material may be silicon, any other single crystal semiconductor, and any combinations thereof. Nanorods have a length from about 100 nm to about 100 microns and a diameter from about 1 nm to about 1 micron. Nanorods may be derivatized with receptor material including, but not limited to, glasses, plastics, polymers, metals, ceramics, insulators, organic materials, inorganic materials, and any combinations thereof. Also, nanorods may be derivatized with material including but not limited to, polymers, proteins, peptides, antibodies, enzymes, nucleic acids, cells, drugs, and any combinations thereof. Substrates are solid phase compositions including, but not limited to, semiconductors, glasses, plastics, polymers, metals, ceramics, insulators, organic materials, inorganic materials, and any combinations thereof. Examples of substrates are silicon, germanium, gallium arsenide, indium phosphide, silicon carbide, sapphire, and any combinations thereof. Aligning derivatized nanorods is by self-assembly, including, but not limited to, electrostatic assembly, capillary assembly hydrophobic/hydrophilic assembly, biomolecular hybridization, and any combinations thereof. Aligning derivatized nanorods may be effected by electric field assisted assembly, magnetic filed assisted assembly, fluidic assembly, and any combinations thereof. Substrates are patterned with circuitry including sensing circuitry, data processing circuitry, data transmission circuitry, and any combinations thereof. In one embodiment, derivatized nanorods are aligned and integrated with at least one electrode of the patterned substrate. In another embodiment, derivatized nanorods are aligned and intergrated between two electrodes of said patterned substate. Integrating derivatized nanorods involves attaching at least one nanorod to circuitry of said patterned substrate. Patterned substrate is preferably a fabricated CMOS design. Substrates may be patterned by lithography, stamping, screen masking, printing or physical modification.

The invention provides a method for selectively analyzing target material of a sample comprising contacting a sample with a nanomechanical transducer comprising: a plurality of integrated nanorods derivatized with receptor material selective for said target material, wherein the nanorods are aligned as integrated nanocantilevers, and a substrate patterned with circuitry providing a detection means; adhering the receptor material with the target material of the sample; and detecting the adherence of the receptor material with the target material, thereby selectively analyzing the target material. The detecting means may detect resonance frequency or static deflection. Also, the method may further add at least one nanoparticle (ie., gold tag), said nanoparticle adheres with said adhered receptor material and said target material. Amplification is effected. The detection means may be capacitive detection, piezoelectric detection, electromagnetic detection, optical detection, or any combinations thereof. Nanorods are conveniently derivatized with receptor material including, but not limited to, glasses, plastics, polymers, metals, ceramics, insulators, organic materials, inorganic materials, and any combinations thereof. The method of claim 19, wherein said plurality of nanorods is derivatized with various materials including polymers, proteins, peptides, antibodies, enzymes, cells, nucleic acids, drugs, and any combinations thereof. Nanorods may be derivatized with a single receptor material for analysis of a single target material in said sample. Also, nanorods may be deriviatized with a plurality of receptor materials for analysis of a plurality of target materials in the analyte or sample. Nanorods are preferably metals, semiconductor materials, insulator materials, dielectric materials, piezoelectric materials, and any combinations thereof. Nanorods may be Au, Pt, Pd, Ag, Pb, Ni, Rh, Co, CdSe, Si, and any combinations thereof. Nanorods may be silicon, any other single crystal semiconductor, or any combinations thereof. Nanorods preferably have a length from about 100 nm to about 100 microns and a diameter from about 1 nm to about 1 micron. Substrate are solid phase compositions such as semiconductors, glasses, plastics, polymers, metals, ceramics, insulators, organic materials, inorganic materials, and any combinations thereof. Substrates may be silicon, germanium, gallium arsenide, indium phosphide, silicon carbide, sapphire, and any combinations thereof.

Samples or analytes may be organic chemical compositions, inorganic chemical compositions, biochemical compositions, cells, microorganisms, peptides, polypeptides, proteins, lipids, carbohydrates, nucleic acids, and any combinations thereof. Samples may comprise target nucleic acid and receptor material nucleic acid which adheres by hybridization with the target nucleic acid. The sample is in the form of a solid, a liquid or a gas. Nanorods are derivatized with materials including, but not limited to, polymers, proteins, peptides, antibodies, enzymes, nucleic acids, drugs, and any combinations thereof. Nanorods may be derivatized with organic materials selected from the group consisting of polymers, proteins, peptides, antibodies, enzymes, nucleic acids, drugs, and any combinations thereof. Nanomechanical transducers or devices of the invention may be integrated with at least one other type of device for analyzing target molecules.

BRIEF DESCRIPTION OF THE DRAWINGS

FIG. 1 is a schematic illustration not drawn to scale of a nanomechanical biosensor of the present invention. FIG. 1A shows a receptor molecule and graph of resonance frequency. FIG. 1B shows receptor molecule adhering or binding selectively with a target molecule and a graph of resonance frequency showing a shift from the resonance frequency of FIG. 1A. Shown are: molecule with specific receptor 1, target molecule 2 that binds selectively to receptor 1, electrode 4, nanorod 3, insulator material 5, and insulator material 6.

FIG. 2 is a schematic representation of the fabrication of heterogeneously integrated biosensor arrays. FIG. 2(a) illustrates derivatizing of nanorods in solution with nanorods having different receptor molecules. FIG. 2(b) shows assembly of rods on a substrate (CMOS electronics). FIG. 2(c) is a SESM of nanorods aligned between two electrodes. Shown are: nanorods with receptor $M_A$ 20, nanorods with receptor $M_B$ 21, nanorods with receptor $M_C$ 22. receptor molecule $M_A$ 23, receptor molecule $M_B$ 24, receptor molecule $M_C$, buried electrode 27, electrode 28, nanorod 29, and CMOS electronics 24.

FIG. 3 illustrates metal nanorod synthesis. FIG. 3(a) shows a template after deposition of Ag backing electrode and initial Ag deposition in pores. FIG. 3(b) shows sequential electodeposition of metals in pores leads to array of striped nanowires. FIG. 3(c) shows dissolution of template and release of striped metal nanowires into suspension. FIG. 3(d) shows an optical microscope image of a nanowire suspension. FIG. 3(e) to FIG. 3(g) show the synthesis of a semiconductor nanorod. FIG. 3(e) illustrates electo-deposition Au catalylst. FIG. 3(f) shows $SiH_4$ introduction. FIG. 3(g) shows dissolving of membrane. FIG. 3(h) shows an Au-tipped Si nanowire and FIG. 3(i) is a high resolution TEM image of a Si nanowire crystal lattice.

FIG. 4 illustrates nanorod derivatization and demonstration of selective DNA assay on functionalized nanowires. FIG. 4(C) is a schematic illustration of the assembly strategy. FIG. 4(A)(1) shows fluorescence indicating that hybridization has occurred on one population of nanowires. FIG. 4(A)(2) shows a reflectance image of all wires present in the filed of view. FIG. 4(B)(i) to FIG. 4(B)(iii) show fluorescence activity.

FIG. 5(a) illustrates an attachment scheme. The Au nanosphere 50 could be used, for example, in place of a fluorescent tag. Each nanosphere will harbor more than one DNA strand (only one is illustrated). FIG. 5(b) shows 200-nm diameter Au wires which have been decorated with 12-nm Au spheres. FIG. 5(c) shows a non-complementary control experiment. When the correct analyte DNA dequence is not present, Au particles do not attach to the nanowire surface. Shown are: Au:DNA conjugate 51, analyte DNA 52, biotinyl DNA 53, NA 54, and nanowire 55.

FIG. 6 illustrates electric field assisted assembly and integration. Shown are: field lines 60, passive electrode 61, $SiO_2$ substrate 62, buried electrode 63, aligned nanowire 64, and top metal contact 65, electrode 66, and nanowire 67.

FIG. 7 illustrates a nanocantilever device and demonstration of its operation. FIG. 7(a) is a cross-sectional view of a nanomechanical device of the invention prior to rod release.

FIG. 7(b) shows the device following rod release. FIG. 7(c) is a SEM image of a fixed-fixed rhodium nanorod; and FIG. 7(d) is a SEM image of a fixed-free rhodium nanocantilever a released rhodium nanorod. FIG. 6(e) is a graph showing the measured resonant frequency of a nanorod cantilever device of the present invention. Shown are metal nanorod 70, electrode 71, 300 nm $SiO_2$ 72, and thermal $SiO_2$ 73.

FIG. 8 illustrates nanorod integration with CMOS electronic circuit. Shown are: drive circuit 80, via to CMOS circuitry 81, passive electrodes 82, buried electrodes 83, local CMOS circuitry 84, drive circuit 85, via to CMOS 86, nanorod biosensor 87, metal interconnect 88, buried electrodes 89, and Si substrate 90.

FIG. 9 is an illustration of a cross-section of a nanocantilever biosensor. Shown are: nanowire 90, electrode 91, electrode 92, insulator material 93, insulator material 94, and insulator material 95. Electrode 91 is snown at 100-500 nm dimension, but may conveniently vary in size (i.e., from about 100 nm-10 microns or more).

DETAILED DESCRIPTION OF THE INVENTION

Figure 5:
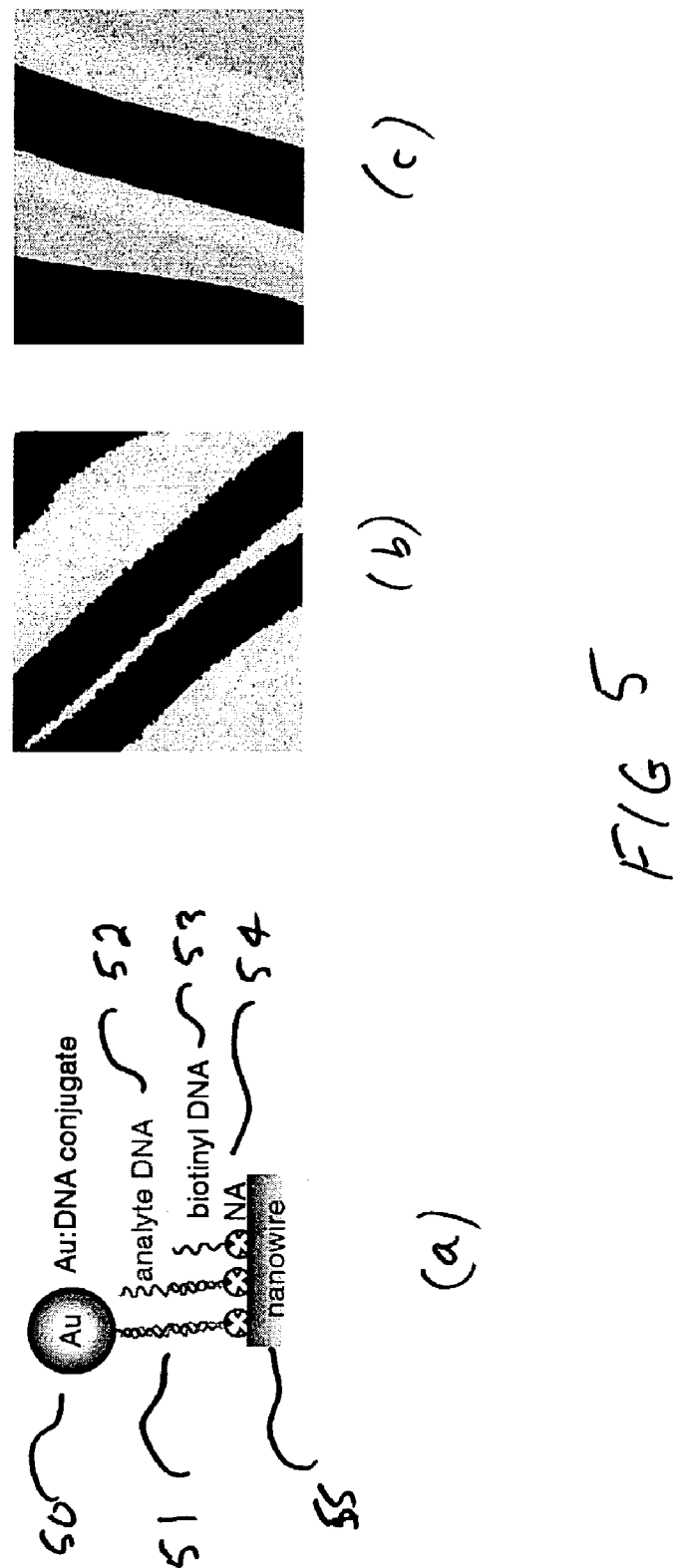
FIG. 5 illustrates nanoparticle amplification; Au nanoparticles can be selectively attached to a nanowire surface in the presence of analyte or sample DNA sequences. For a 12-nm diameter particle, the mass change for a single particle binding event can be significant.

The present invention provides biosensor arrays based on mass-sensitive nanomechanical biosensors that are integrated onto silicon or thin film electronic chips using the provided bottom-up methodology. The nanomechanical biosensor transducers of the present invention do not have obligatory requirements for optical excitation or detection; nanocantilever deflections may be measured on chip via a direct electrical response using one of several methods. In a preferred embodiment, piezoelectric materials are incorporated onto the nanorods. Here, the voltage difference developed across the piezoelectric material that is proportional to the strain induced on the piezoelectric material can be readily detected by on-chip interface electronics.

In the biosensors of the present invention, where the transducer in the dynamic mode senses a shift in resonant frequency due to receptor-target binding, the transducer sensitivity improves as the ratio of the cantilever surface area to mass increases (c.f., FIG. 1). Using the mass-sensitive approach, it is estimated that these nanomechanical transducers are able to detect mass changes on individual 200-nm diameter wires that correspond to single target-receptor binding events (i.e., molecular level) using functionalized 12-nm Au nanoparticle target probes. Mass changes corresponding to hybridization of $3.2 \times 10^{10}$ DNA strands/cm$^2$ (1200 strands/wire) are also expected to result in measurable shifts in resonant frequency without using nanoparticle probes.

When the transducers of the present invention are in the static mode where the transducer senses a deflection in the cantilever beam due to receptor-target binding, the transducer sensitivity improves as the surface area of the cantilever decreases. This provides enhanced sensitivity of these transducers over silicon micromachined cantilevers. The ability to measure static deflection may be advantageous for use in liquid environments where damping of the mechanical resonance may become significant.

The biosensor transducers of the invention provide direct quantitative information on the concentration of biomolecule targets in a sample population, since the shift in resonance frequency or static deflection is directly proportional to the number of receptor-target binding events. In addition, because biosensor transducers of the invention are compatible with nanoparticle target probes, these biosensors will provide excellent hybridization selectivity to single-base pair DNA mismatches.

The biosensor transducers of the invention are compatible with converting mechanical deflections into electrical signals using piezoelectric tipped or coated nanorods, capacitive coupling, or electromagnetic coupling leading to complete on-chip integration of sensing and data processing functions.

The "bottom-up" integration or methodology of the present invention permits large-scale parallel integration of a large number of transducers capable of sensing different targets in a single analyte solution (c.f., FIG. 2). It also permits integration of the nanomechanical transducers onto a variety of substrates, including, but not limited to, insulators such as glass and various polymers. Bottom up assembly, as used herein, is defined as transferring nanorods synthesized in large quantity to a patterned substrate. This bottom-up assembly is in contrast to top-down fabrication techniques of the art where cantilever structures are fabricated directly on the substrate using conventional top down semiconductor processing steps. Bottom-up assembly provides systems having integrated heterogeneous sensors (i.e., derivatized nanorods with different receptor coatings) on a chip in parallel arrangement. In the case of nucleaic acid (DNA/RNA) derivitization, the present invention provides unparalled detection selectivity, while the nanometer-scale dimensions of the resonant cantilevers of the invention provide extremely high detection sensitivity. The bottom-up methodology of the invention also provides for the incorporation of various materials onto the ends of the nanorods, including, for example, piezoelectric materials, enabling measurement of changes in resonance shifts by electrical readout of integrated nanocantilevers In view of the fact that receptor molecules are preferably integrated onto the nanorod prior to alignment, serial methods for derivatizing the biosensor transducers following fabrication are eliminated reducing manufacturing time. This also provides improved detection selectivity towards different targets in a single analyte solution because the change of cross contamination during nanorod derivitization is not present.

The present invention uses template replication techniques to grow $\sim 10^9$, 30-200 nm diameter metal or silicon nanorods in each synthetic run. DNA may be attached to metal nanorods in solution by nonspecific direct adsorption (e.g., of proteins) or more specific metal-adsorbate interactions such as those that occur in alkanethiol self-assembled monolayers (i.e., for assembly of thiolated oligonucleotides or of aminated alkanethiols for covalent attachment of biomolecules). The nanorods may be integrated on-chip using bottom-up electrofluidic alignment methodology that can be "programmed" to place nanorods with different DNA at specific locations on a silicon wafer with micron-scale precision. We may detect extremely small mass changes due to DNA hybridization by measuring the shift in resonant frequency of the nanocantilevers. Preferably, this will be done with piezoelectric materials to convert mechanical deflections into electrical signals that can be sensed on-chip. Alternatively, optical detection may be conveniently used.

Calculations show that nanomechanical transducers of the invention report mass changes that correspond to approximately $10^{10}$ DNA strands/cm$^2$ (600 strands/wire assuming a 24-base sequence binding to a 100 nm diameter, 6 micron long, Si wire coated with thiolated 12-base DNA) with frequency shifts on the order of 100 Hz. We note here that 10's of Hz are detectable for resonators with high Q, and that longer strands of DNA will lead to greater mass changes. The nanomechanical biosensor will also provide direct quantitative information on the concentration of biomolecule targets in the sample population, since the shift in resonance frequency is directly proportional to the mass change, and hence the number of DNA hybridization events. Sensitivity can be further improved by incorporating an Au nanoparticle mass tag. The binding of a single 12-nm Au:DNA conjugate will give the same mass change as 1200 DNA strands. Thus this method could ultimately give single molecule sensitivity (i.e. when the binding of one Au:DNA conjugate corresponds to the binding of one analyte DNA strand).

Most of the planar on-chip biosensors of the art integrate biomolecules by attaching them to particular sensing elements during wafer fabrication using mechanical spotting, lithographic, or ink jet approaches. These top-down analyte recognition methods of chip fabrication and biomolecular integration limit the density and reduction in cost possible for future biosensor arrays. The use of bottom-up nanorod integration and electrical readout strategies of the present invention will open the door to high-density integration with each sensor in the array occupying chip areas as small as 3 µm$^2$ (i.e., 3 µm long nanorods with 1 µm pitch between adjacent sensors). This can be used to either provide (1) sensor redundancy on arrays used for limited target, or (2) a large number of receptor variations on arrays used for gene recognition. Finally, by combining the electronic signal processing power of silicon with these highly sensitive nanomechanical biomolecular transducers, it is possible to have single chip biosensors that are at least as sophisticated as today's much larger and more expensive systems. Also, the nanomechanical cantilever transducers of the invention provide real-time responses, and can, for example, be used to collect data remotely via wireless data transmission.

Synthesis of Nanorods

The synthetic approach of the invention producing the nanorods may use template replication procedures where metals are electrodeposited and semiconductors are grown via vapor-liquid-solid (VLS) deposition in mesoporous membranes fabricated by anodization of Al to Al$_2$O$_3$. (c.f., FIG. 3) The template replication technique can produce in excess of 10$^{11}$ identical nanometer-scale rods in one electrodeposition process. The pore diameter and spacing can be varied and has been used to produce wires with diameters ranging from 30-300 nm, and lengths of 1-10 µm. The nanorods can be single metals, semiconductors, dielectrics or insulators, or striped multi-material where the length of the stripes can be controlled with excellent precision. Nanorods prepared via either method can be released from the membrane by selective chemical etching and suspended in a solvent for DNA, or other biochemical/chemical, attachment and assembly. An example of this template approach is more fully described in PCT publications WO0125510 and WO0125002 hereby incorporated by reference. Nontemplate techniques could also be used to synthesize the nanorods.

FIG. 3A illustrates a procedure for metal nanorod synthesis by templated electrodeposition. This technique is routinely used to prepare a wide variety of nanorods. For application as mass-sensitive nanocantilevers, it is desirable to prepare low mass, high-aspect ratio particles. Thus, long rods with small diameter (e.g. 30-nm diameter) synthesized from lower-density materials are preferred. Any of the materials listed in Table I are possible choices for nanorod composition.

TABLE I

| Material (g/cm$^3$) | Densities Density |
|---|---|
| Au | 19.3 |
| Pt | 21.5 |

TABLE I-continued

| Material (g/cm$^3$) | Densities Density |
|---|---|
| Rh | 12.4 |
| Ag | 10.2 |
| Pd | 11.4 |
| Co | 8.9 |
| CdSe | 5.81 |
| Si | 2.3 |

Ultimately, selection of nanorod composition will depend not only on mass, but also on other properties including surface chemistry, mechanical integrity, stability, and ease of alignment. For example, while the density of Au is quite high, the surface chemistry for DNA attachment has already been developed for Au particles (see below). Crystallinity of the metal wires also plays an important role in determining mechanical properties of the nanocantilever. Single crystal Au, Ni, Cu, and Sn nanorods may be produced by elelctrodeposition.

FIG. 3B illustrates an approach to preparing Si nanorods using vapor liquid solid growth using a template directed strategy. Single crystal silicon nanorods with high aspect ratio can be produced using this technique. With the crystallinity and lower density of Si, these wires as well as other single crystal semiconductor or oxide nanorods may be a better choice for biosensor nanocantilevers in comparison to the metallic nanorods described herein.

Nanorod Derivatization

Derivatization chemistries for metal surfaces and metal nanoparticles range from nonspecific direct adsorption (e.g., of polymers or proteins) to more specific metal-adsorbate interactions such as occur in alkanethiol self-assembled monolayers. This rich chemistry enables the coupling of a wide variety of biological receptor onto metal nanorods.

To demonstrate that nanorods can be used as supports for bioassays, we have adapted DNA hybridization and immunoassays for use on these particles. FIG. 4A shows a multiplexed "sandwich" hybridization assay conducted on nanorods where three different populations of nanorods with different Au/Ag striping patterns were derivatized with three different 12-mer "capture" oligonucleotide sequences, each complementary to a known 24-mer target sequence. A solution containing one of the three possible target sequences is added, followed by addition of three Texas red-labeled 12-mer "detection" sequences complementary to the overhanging regions of the possible target DNAs. Analyte binding is observed via fluorescence (center), and identified based on the reflectivity pattern (right) of the nanorods that also appear in the fluorescence image. The particles that showed up in the fluorescence image can be identified as those with the pattern Ag—Au—Ag (labeled with "1" in the images). These data indicate the presence of the target sequence against which particles of type 1 were prepared, and demonstrate selective DNA hybridization to nanorods derivatized with complementary sequences.

These chemistries may be adaptable for attachment of oligonucleotides onto Si nanorods. It may be possible to directly adsorb neutrAvidin to the Si nanorod surfaces as we do for metal surfaces; however protein adsorption to the native oxide surface may not be as favorable as to Au. We will use organosilane chemistry to derivatize the native oxide on the Si nanorods with reactive functional groups for covalent attachment to endgroups on the 3' or 5' terminus of the oligonucleotides. For example, amines can be reacted with carboxylates to form amides using standard carbodiimide chemistry (i.e., EDC/NHS ester).

Oligonucleotides may be attached to the nanorods following release from the membrane and prior to integration on the silicon substrate. Nanorods with different DNA sequences will be integrated either serially or in parallel to form dense arrays of resonators that can be addressed individually, as described in a later section.

In practice, after measuring and storing the resonant frequency of each cantilever, the chip would be exposed to a target DNA and the resonant frequency of each device measured and compared to the starting value. The change in frequency will be related to the presence and concentration of the target DNA. The DNA sequences typically used are quite short, with molecular masses of 3,841 g/mol for the 12-mer sequence and 9,108 for the 24-mer. We estimate the order of magnitude of the nanorod mass change to be approximately 0.01% for $10^{10}$ 24-mer DNA molecules/cm$^2$ (i.e., 600 molecules/wire) binding to a 100-nm diameter, 6 micron long Si wire, following hybridization at low concentrations of analyte DNA in solution. Note that the maximum concentration of binding sites on the nanorod surface will be approximately $10^{13}$ sites/cm$^2$. Preliminary calculations on undamped cantilevers with 100 nm diameter silicon wires suggest that this mass change will result in an easily detectable change in resonant frequency. Longer DNA sequences and/or Au nanoparticle amplification can also be used to increase the mass change for each strand of DNA that hybridizes.

Nanoparticle Amplification:

For very low concentrations of target analyte, it may be desirable to further increase the mass change per binding event. This can be accomplished by conducting a "sandwich" hybridization assay, analogous to that in FIG. 5, but replacing the fluorescent tag with a 12-nm Au nanoparticle. We have used particle-amplification strategies similar to this to improve detection limits in a surface plasmon resonance (SPR) assay. In these experiments, the detection limits were increased three orders of magnitude over the unamplified event. Although many sizes of monodisperse Au particles can be prepared, we have the most experience with 12-nm diameter Au particles. FIG. 5 shows TEM images for 12-nm Au nanoparticles bound to Au nanorods via selective DNA hybridization. The nanorod on the left was exposed to DNA: Au conjugates that were not complementary to the DNA on the wires. Very low nonspecific adsorption of Au nanoparticles was observed in these experiments. The expected mass change for binding a single 12-nm diameter Au particle to a 100-nm diameter, 6 μm long Si nanorod is $1.8 \times 10^{-17}$ g. Preliminary calculations indicate substantial frequency shifts for this mass change, e.g. for Si nanorods, a frequency shift of approximately $10^3$ Hz is predicted. Frequency shifts of □100 Hz can be measured, therefore, it should be possible to detect single DNA binding events via this technique.

Heterogeneous Integration of Derivatized Nanorods

One of the key advantages of the nanorod-based sensors is the promise of large-scale parallel integration of the biosensors arrays directly onto fully processed silicon or thin film electronic chips. The foundation of this approach is the ability to produce bulk quantities of biosensors derivatized with different receptors, and then transfer them in parallel to the silicon chips using advanced bottom-up heterogeneous integration schemes. This removes many of the constraints associated with current top-down biosensor integration strategies, including potential process incompatibilities, time-consuming serial integration, and large sensor area.

One possible assembly method employs an electrofluidic assembly process that uses a combination of long- and short-range forces to attract nanorods from suspension and align them between pairs of lithographically defined passive electrodes. The long-range attraction and orientation results from dielectrophoretic forces induced on the highly polarizable nanorods in a nonuniform electric field, which is produced by energizing buried electrodes with an AC voltage as shown in FIG. 6. As a result of the strong capacitive coupling between the energized and passive electrodes, the highest field strength is observed at the periphery of the top passive electrodes. As the nanorods approach the passive electrodes with spacing approximately equal to the length of the nanorods, the electric field strength between the passive electrodes and the nanorod tips increases proportionally to the inverse of the distance from the electrodes. It is this large near-field force that results in final alignment of individual nanorods between pairs of top passive electrode pads. We have shown that the nanorods remain firmly attached to the substrate following alignment, which permits us to use standard optical lithography to define contacts or anchors at the tips of the nanorod (FIG. 6). These contacts are used as electrical connections to the nanorods and mechanical connections to the substrate.

Bottom-up integration strategies should be compatible with DNA-derivatized nanorods. The greatest attachment chemistry to prevent the DNA from desorbing from the nanorods during electrofluidic assembly, (2) developing approaches to minimize deleterious effects that may result when the DNA are removed from buffer solutions and dried following alignment, and (3) developing biomolecular compatible (non)lithographic techniques that can be used to fabricate rigid supports at the nanorod tip(s).

Nanomechanical Metal Rod Cantilevers

Metal rods fabricated by template replication were assembled onto a substrate that was designed to facilitate nanomechanical measurements. In particular, as shown in FIG. 7, the metal rods were aligned between two electrodes that were deposited on a 300 nm thick layer of PECVD SiO$_2$. In addition to providing electrical isolation between the top and bottom field pads, this SiO$_2$ layer served as a sacrificial layer during cantilever release. Large area metal pads were deposited on both ends of the rods to provide a rigid contact to the substrate. The rods were released by dissolving the SiO$_2$ in buffered HF (e.g. 10:1 buffered HF for 45 s). The samples were packaged and characterized to determine the resonant frequency. The results of the resonant frequency characterization are shown in FIG. 6 for a rod cantilever rigidly attached to the substrate on both ends. As is evident from this data, the cantilever resonance is well defined, but is rather broad. We believe that this is due to the polycrystalline nature of the metal rods, and is not an inherent limitation of these nanomechanical resonators. If the biosensor transducer is operated in the dynamic mode it is the change in the resonant frequency of the metal rod cantilever that will be used to sense the binding of receptor and target molecules. A similar approach can be used to monitor the static deflection of the nanomechanical cantilever. Note that while we reference throughout this application the use "receptor molecules" to coat the metal rods, strictly speaking any material with the capability of attaching to a target can be used. This includes certain polymers that are known to those skilled in the art.

BioSensor Arrays

Single BioSensor Transducer: Consider a suspended metal or semiconductor rod with specific receptor molecules adsorbed to the surface of the rod as shown in FIG. 1. This device will have a characteristic resonant frequency that depends on the length, diameter, and stiffness of the rod as well as the mass of the adsorbed monolayer of receptor molecules. When this device is placed in an environment where it is exposed to the complementary target molecule, the target molecule will bind to the receptor as illustrated in FIG. 1 and will cause a change in the resonant frequency of the nanomechanical cantilever due to the change in the mass of the transducer. In this example, the environment could be either air or liquid (solution). The change in resonant frequency can be detected either optically or electrically and analyzed to register the binding event and to provide quantitative information regarding the concentration of the target molecule in the environment. Molecule specificity (or selectivity) is obtained through selection of the appropriate receptor molecules that only bind to the target molecule of interest. Therefore, two or more devices with different receptor molecules, $M_A$ and $M_B$, will only register a binding event when they bind with their complementary target molecule, $M_A'$ and $M_B'$.

BioSensor Array: A biosensor array can be fabricating by designing a platform that permits integration of the electronics required for sensing and analysis with an dense array of individual biosensor transducers. In this approach, the platform on which the sensors are integrated is arbitrary. In particular, high-performance transducers can be integrated onto single crystal silicon CMOS platform to take advantage of the circuit performance attributes that this material system offers. In contrast, transducers could also be integrated onto alternative (arbitrary) substrates including glass, ceramics, polymers, etc. using thin-film electronic circuits. These may offer advantages for sensors that must operate in harsh environments.

Because the individual biosensor transducers are integrated using a bottom-up rather than top-down approach, it is possible to adsorb the receptor molecules prior to integrating the metal or semiconductor rod on the computational platform. This has the advantage that rods can be functionalized with different receptor molecules simultaneously prior to assembly, eliminating the need to "dip" each chip into the molecular assembly solutions following device fabrication. This should reduce cost and improve binding selectivity because there is no post-fabrication molecule adsorption. It is possible to envision a large number of array configurations, but perhaps the simplest configuration would be an array comprised of columns or rows of discrete devices, where all of the rods in each row or column would be functionalized with the same receptor molecule with adjacent rows of columns comprised of rods each with different molecules. The most obvious approaches for rod assembly would include electro-fluidic or pure fluidic assembly. In the case of electrofluidic assembly, each row or column would be biased during the assembly process, which would result in the rods being aligned to that particular column and not adjacent columns. For pure fluidic assembly (and possible electrofluidic assembly), a flow cell would be used to direct the functionalized rods along each row or column. This biosensor array would introduced a large degree of redundancy, which would overcome potential limitations in yield associated with the rod assembly. Moreover, the redundancy would also reduce the chance of false targets by permitting analysis over large numbers of sensors aimed at selecting a single molecule.

Electrical sensing can be achieved by integrating an additional lithographically defined feature on the circuit platform prior to rod integration. In particular, it is possible to integrate a metal pad below the suspended rod cantilever to sense the change in resonant frequency. A cross-section of this device, showing the CMOS integration is illustrated in FIG. 8. A variety of sensing circuits can be used to measure the change in resonant frequency. Examples of sensing circuits can be found by surveying the literature on tuning fork Atomic Force Microscopes as well as information available on silicon micro and nano-resonators. Examples include capacitive sensing of the cantilever deflection, which may be limited because of the extremely small capacitances that are being sensed. A second alternative is based on piezoelectric sensing of the cantilever deflection. Here a tip of the nanorod could be coated with a thin film piezoelectric material. In a fixed-fixed cantilever configuration, a voltage will be developed across the piezoelectric film that is proportional to the strain induced on the piezoelectric material. Because the deflection strains are large, large voltages should be generated.

Molecule Selection

The molecules that are selected for this application must have the following properties: (1) Molecules $M_A$, $M_B$, $M_C$, etc. are able to bind to the metal or semiconductor nanorod. Examples of binding chemistries include those based on alkanethiol or isonitrile self-assembled monolayers, and direct adsorption (e.g. of proteins or polymers). (2) Molecules $M_A$, $M_B$, $M_C$, etc. can be designed and synthesized to serve as a selective receptor to their respective target molecules. Examples include DNA oligonucleotides and peptide nucleic acid (PNA) oligonucleotides, which can be synthesized to order for complementarity to desired targets. In addition, antibodies are commercially available for many proteins and can be produced against desired antigens for which no commercial antibody exists. (3) Molecules $M_A$, $M_B$, $M_C$, etc. must be robust enough to withstand post-processing and function as good receptors in the sensor environment.

EXAMPLE

Nanorod Integration Process

Several nanorod integration schemes are possible. Here, we will provide a process flow for one scheme that can be used for molecule assembly onto the rods prior to their integration. This process flow is outlined in FIG. 1. There are many other schemes that could be envisioned for those who are skilled in the art of process integration. These involve assembling the rods prior to molecule integration and assembling the molecule using orthogonal assembly onto different metal rods OR through electric-field enhanced assembly of the molecules.

Step 1-Rod Synthesis: Using the template replication approach described previously, we synthesize rods and suspend them in a solvent that is compatible with molecule assembly.

Step 2-Receptor Molecule Assembly: In this example, we have three vials of rods with different receptor molecules $M_A$, $M_B$, and $M_C$ in each vial. Using template replication techniques, we synthesize and functionalize >$10^{11}$ rods simultaneously. The rods synthesized using this approach are so plentiful that they can be used to fabricate devices on a large number of arrays and substrates. We use both SAM-based chemistry and direct adsorption of proteins like neutravidin, which adsorbs nonspecifically to the particles and has tight binding sites for a small molecule, biotin, which can be used as an anchor for a molecule of interest. For example, oligonucleotides synthesized with a 5' biotinyl group will attach to the particle via the NA such that the DNA is only attached via this end of the molecule, leaving the rest of the molecule (i.e. the bases) available for hybridization to their complement.

Step 3-Integration onto Substrate Containing Sensing and Analysis Circuitry: Electro-fluidic or Fluidic Assembly is used to align rods from each vial along one column of the array. This process is repeated for each vial of rods until the array is completed. In the case of fluidic assembly (or combined electro- and fluidic assembly), it may be possible to align in parallel rods from all vials by designing multi-channel flow cells. Following assembly, the alignment fluid must be removed and the sample must be dried. This step must be developed to minimize the impact on the receptor molecules, which may be sensitive to their local environment.

Step 3a-Design of Alignment Pads: The alignment pads discussed in the background will be suspended by the amount required to separate the sample from the substrate. Previous experiments have demonstrated that the rods align to the tops of the pads, eliminating the need for a release step that might be destructive to the receptor molecules. An example of the cross section is shown in FIG. 9.

Step 4-Post-Assembly Rod integration with Sensing Circuitry: The tips of the aligned rods must rigidly attached to the substrate. This can be accomplished using standard microfabrication techniques. Because the molecules may be sensitive to photoresist and solvents used in these processes, we may resort to shadow masking metal on the tips of the rods. This step can also be used to interconnect the rods to the underlying sensing and analysis circuitry if necessary.

Currently, we fabricate rigid supports with metal liftoff or electrodeposition processes that is common in semiconductor manufacturing methods. This process begins by spinning photoresist containing organic solvents onto the sample and softbaking between 70 and 115° C. to remove the solvent. The sample is then exposed through a mask to UV (note that the mid-section of the suspended wire is protected by the mask, so the DNA is never exposed to UV) and is developed in an aqueous base.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. A method for producing a nanomechanical device comprising: derivatizing at least one nanorod with a receptor material to produce at least one derivatized nanorod; applying onto a patterned substrate said at least one derivatized nanorod; aligning electrofluidically said at least one derivatized nanorod with long-range dielectrophoretic and short-range electrostatic forces to attract said at least one derivatized nanorod onto said patterned substrate, said patterned substrate defining passive electrodes and buried electrodes, wherein said buried electrodes produce said dielectrophoretic forces, and said electrostatic forces occur between said passive electrodes and said at least one derivatized nanorod; and integrating said at least one derivatized nanorod with said patterned substrate to form an integrated nanocantilever structure, thereby producing a nanomechanical device by bottom-up assembly, wherein said bottom-up assembly transfers said derivatized nanorods synthesized in large quantity by parallel assembly onto a patterned chip by: off-chip nanorod synthesis and molecule derivatization; assembly of said derivatized nanorods onto said patterned chip containing sensing and analysis circuitry with registration with respect to said circuitry on said patterned chip; and post-assembly integration of said derivatized nanorods with said circuitry on said patterned chip.

2. The method of claim 1, wherein said at least one nanorod is selected from the group consisting of: metals, semiconductor materials, insulator materials, dielectric materials, piezoelectric materials, and any combinations thereof.

3. The method of claim 1, wherein said at least one nanorod is a material selected from the group consisting of Au, Pt, Pd, Ag, Pb, Ni, Rh, Co, Cd, Se, Si, and any combinations thereof.

4. The method of claim 1, wherein said at least one nanorod is a material selected from the group of: silicon, any other single crystal semiconductor, and any combinations thereof.

5. The method of claim 1, wherein said at least one nanorod has a length from about 100 nm to about 100 microns and a diameter from about 1 nm to about 1 micron.

6. The method of claim 1, wherein said at least one nanorod is derivatized with receptor material selected from the group consisting of: glasses, plastics, polymers, metals, ceramics, insulators, organic materials, inorganic materials, and any combinations thereof.

7. The method of claim 1, wherein said at least one nanorod is derivatized with material selected from the group consisting of polymers, proteins, peptides, antibodies, enzymes, nucleic acids, cells, drugs, and any combinations thereof.

8. The method of claim 1, wherein said substrate is a solid phase composition selected from the group consisting of semiconductors, glasses, plastics, polymers, metals, ceramics, insulators, organic materials, inorganic materials, and any combinations thereof.

9. The method of claim 1, wherein said substrate is selected from the group consisting of: silicon, germanium, gallium arsenide, indium phosphide, silicon carbide, sapphire, and any combinations thereof.

10. The method of claim 1, wherein aligning at least one derivatized nanorod is by self-assembly.

11. The method of claim 1, wherein said substrate is patterned with circuitry selected from the group consisting of: sensing circuitry, data processing circuitry, data transmission circuitry, and any combinations thereof.

12. The method of claim 1, wherein said at least one derivatized nanorod is aligned and integrated with at least one electrode of said patterned substrate.

13. The method of claim 1, wherein said at least one derivatized nanorod is aligned and integrated between two electrodes of said patterned substrate.

14. The method of claim 11, wherein integrating said at least one derivatized nanorod comprises attaching said at least one nanorod to said circuitry of said patterned substrate.

15. The method of claim 1 wherein said patterned substrate is a fabricated CMOS design.

16. The method of claim 1, wherein said substrate is patterned by lithography, stamping, screen masking, printing or physical modification.

* * * * *

UNITED STATES PATENT AND TRADEMARK OFFICE
CERTIFICATE OF CORRECTION

PATENT NO. : 7,655,269 B2　　　　　　　　　　　　　　　　　　　　　　　Page 1 of 1
APPLICATION NO. : 10/423832
DATED : February 2, 2010
INVENTOR(S) : Mayer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this

Twenty-third Day of November, 2010

David J. Kappos
*Director of the United States Patent and Trademark Office*